(12) United States Patent
Meyer et al.

(10) Patent No.: US 7,390,930 B2
(45) Date of Patent: Jun. 24, 2008

(54) PREPARATION OF KETALS

(75) Inventors: Oliver Meyer, Muenster (DE); Renate Uhlenberg, Recklinghausen (DE); Michael Korell, Denville, NJ (US)

(73) Assignee: Degussa AG, Duesseldorf (DE)

( * ) Notice: Subject to any disclaimer, the term of this patent is extended or adjusted under 35 U.S.C. 154(b) by 832 days.

(21) Appl. No.: 10/619,436

(22) Filed: Jul. 16, 2003

(65) Prior Publication Data

US 2004/0152920 A1 Aug. 5, 2004

(30) Foreign Application Priority Data

Feb. 1, 2003 (DE) ............................... 103 04 055

(51) Int. Cl.
*C07C 223/00* (2006.01)
(52) U.S. Cl. ..................................................... 564/502
(58) Field of Classification Search ................. 524/102; 564/502; 544/406
See application file for complete search history.

(56) References Cited

U.S. PATENT DOCUMENTS

| | | | | | |
|---|---|---|---|---|---|
| 3,790,525 | A | * | 2/1974 | Kurumada et al. | ............ 524/99 |
| 3,839,273 | A | * | 10/1974 | Murayama et al. | ............ 524/99 |
| 3,862,100 | A | * | 1/1975 | Halasa et al. | ................ 526/181 |
| 3,940,401 | A | | 2/1976 | Murayama et al. | |
| 3,959,298 | A | * | 5/1976 | Murayama et al. | .......... 546/242 |
| 3,963,730 | A | | 6/1976 | Murayama et al. | |
| 4,250,312 | A | | 2/1981 | Nakahara et al. | |
| 5,917,059 | A | * | 6/1999 | Bruchmann et al. | .......... 549/372 |
| 6,852,860 | B2 | * | 2/2005 | Weerawarna et al. | .......... 546/16 |
| 2005/0256312 | A1 | * | 11/2005 | Osterholt et al. | .............. 546/16 |

FOREIGN PATENT DOCUMENTS

| | | | |
|---|---|---|---|
| JP | 56-025185 | * | 3/1981 |
| WO | WO02/22593 | * | 3/2002 |

* cited by examiner

*Primary Examiner*—Yvonne Eyler
*Assistant Examiner*—MLouisa Lao
(74) *Attorney, Agent, or Firm*—Oblon, Spivak, McClelland, Maier & Neustadt, P.C.

(57) ABSTRACT

The invention relates to a process for ketalizing triacetonamine by reacting triacetonamine and a hydroxyl derivative, for example, a mono- or polyhydric alcohol, with gaseous hydrogen chloride to give an open-chain or cyclic ketal.

23 Claims, No Drawings

PREPARATION OF KETALS

BACKGROUND OF THE INVENTION

1. Field of the Invention

The present invention relates to an improved process for preparing cyclic and open-chain ketals, in particular of triacetonamine.

2Description of the Background

The ketalization of triacetonamine (2,2,6,6-tetramethyl-4-piperidone, TAA) with mono- or polyhydric alcohols to give the corresponding open-chain or cyclic ketals is known in principle from the literature. For instance, the synthesis of various TAA ketals is described, inter alia, in DE 22 03 533, DE 23 53 538, CS 272 639, U.S. Pat. No. 3,790,525, U.S. Pat. No. 3,940,401, EP 0 222 512, EP 0 291 238 and EP 0 141 502. The catalysts used are those acids known to those skilled in the art for this type of reaction, such as aqueous hydrochloric acid, sulfuric acid, phosphoric acid or various sulfonic acids (usually p-toluenesulfonic acid). Since the ketalization of TAA already uses one acid equivalent for the neutralization of the secondary amine function, a superstoichiometric amount of acid always has to be used, unlike in the case of neutral compounds. A small excess of catalyst is therefore necessary for the reaction in every case.

In addition, there are examples in the literature which do not start from TAA itself, but rather from its hydrochloride (Monatsh. Chem. 93, 1962, 1090-1106; Scripta Fac. Sci. Nat. Univ. Masaryk. Brun., Vol. 23, 1993; JP 56 138 189; JP 56 025 185). This TAA hydrochloride is then converted to the ketal in a similar manner to the abovementioned examples after adding a catalyst acid and the particular alcohol. However, this procedure means an additional synthesis and isolation step, which is of little advantage for the industrial scale production of TAA ketals.

In addition, the ketalization of TAA hydrochloride and a sulfonic acid salt of TAA have also been described by reaction with an orthoester (EP 0 748 849) and by transketalization (U.S. Pat. No. 4,250,312, JP 55 092 386, EP 0 748 849).

One use of the ketals of TAA is as stabilizers in the polymer field. In addition, the corresponding N-oxyl radicals are accessible from them by oxidation of the secondary amine function, and can in turn be used as an oxidation catalyst, as polymerization inhibitors or as mass regulators in polymerizations.

SUMMARY OF THE INVENTION

It is an object of the invention to provide a process for preparing open-chain or cyclic ketals, in particular of triacetonamine, which does not have the abovementioned disadvantages and which in particular starts from simple starting compounds, does not require any additional synthesis and isolation steps and can be carried out without any problems on an industrial scale.

DETAILED DESCRIPTION OF THE PREFERRED EMBODIMENTS

It has been found that, surprisingly, triacetonamine can be reacted with hydroxyl derivatives having one or more hydroxyl groups, in particular mono- or polyhydric alcohols, and with gaseous hydrogen chloride without any undesired side reactions, for example chlorination of the hydroxyl group, taking place to a significant extent.

The invention therefore provides a process for preparing ketals by reacting triacetonamine with hydroxyl derivatives having one or more hydroxyl groups and with gaseous hydrogen chloride to open-chain or cyclic ketals.

The invention relates in particular to a process for preparing cyclic and open-chain ketals of triacetonamine of the formulae:

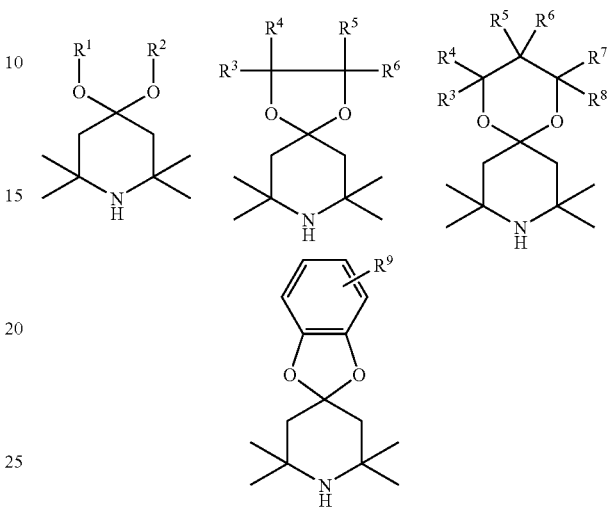

where $R^1$ and $R^2$ are each independently an alkyl group having from 1 to 10, preferably from 1 to 6, carbon atoms, an alkoxyalkyl group or a benzyl group, $R^3, R^4, R^5, R^6, R^7$ and $R^8$ are each independently hydrogen, an alkyl group having from 1 to 10 carbon atoms, a hydroxymethylene group (—CH$_2$OH), an ester function (—CO$_2$R$^1$), a halomethylene group (—CH$_2$—X), an alkoxymethylene group (—CH$_2$OR$^1$), an esterified alkoxymethylene group (—CH$_2$O$_2$CR$^1$), an alkoxyalkyl group, a benzyl group and $R^9$ is a hydrogen, an alkyl group having from 1 to 10 carbon atoms, halogen or an alkoxy group (—OR$^1$).

The present invention also provides methods of producing polymers incorporating the herein described process of ketalizing triacetonamine and adding the resultant open-chain or cyclic ketal to the polymerization reaction.

In the process according to the invention, triacetonamine and a hydroxyl derivative having one or more hydroxyl groups, in particular mono- or polyhydric alcohols, is reacted with gaseous hydrogen chloride. A further catalyst acid is not required.

When carrying out the process according to the invention, it is found that, completely unexpectedly, as early as during the introduction of the gaseous hydrogen chloride and therefore before the complete saturation of the secondary amine function, triacetonamine or the triacetonamine hydrochloride formed in situ are converted to the particular triacetonamine ketal. Although the reaction mixture therefore only has the acidic pH required for a ketalization toward the end of the hydrogen chloride uptake, the triacetonamine conversion at this time for most triacetonamine ketals is surprisingly at 80-95%. It is also possible to use the gaseous hydrogen chloride in a superstoichiometric amount. If desired, the water of the reaction formed in the ketalization can also be subsequently removed from the system, preferably by azeotropic distillation, and the conversion completed in this way.

After neutralization of the reaction mixture and appropriate workup (for example by distillation or filtration and washing), the particular triacetonamine ketals are obtained in high yield and in high purity.

To ease the stirrability in the reaction, a solvent inert toward hydrogen chloride can be added to the mixture. Suitable solvents include acyclic (aliphatic) hydrocarbons, for example heptane, cyclic (cycloaliphatic) hydrocarbons, for example cyclohexane or ethylcyclohexane and in particular aromatic hydrocarbons, for example toluene or xylene, which can also serve after the reaction as azeotroping agents for the removal of the water formed in the reaction.

The reaction is generally carried out between about 20 and about 150° C., preferably between 40 and 120° C. and most preferably between 50 and 90° C.

The reaction is preferably carried out at atmospheric pressure. However, it is also possible to optionally carry out the reaction at a slightly reduced pressure (based on atmospheric pressure) or increased pressure up to preferably 10 bar.

The ratio of triacetonamine to monovalent hydroxyl compound is from 1:2 to 1:8, preferably from 1:2 to 1:4.

The ratio of triacetonamine to polyhydric (at least 2) hydroxyl compound is from 1:1 to 1:4, preferably from 1:1 to 1:2.

Toward the end of the introduction, the amount of hydrogen chloride is superstoichiometric, i.e. at least 1:1, based on the triacetonamine.

Useful hydroxyl compounds include alcohols, hydroxycarboxylic acids, hydroxyketones, enols and phenols, but in particular mono- and polyhydric alcohols. The most important alcohols are in particular 1,2-ethanediol (1,2-ethylene glycol), 1,2-propanediol, 1,3-propanediol, 1,2-butanediol, 1,3-butanediol, 1,2-hexanediol, 1,2,3-propanetriol(glycerol), benzyl alcohol and pyrocatechol and derivatives.

The reaction can be carried out batchwise, semibatchwise or continuously.

As a consequence of the subsequent addition of the gaseous hydrogen chloride, the preferred method is a batchwise method with regard to the triacetonamine and the hydroxyl derivative and a semibatchwise method with regard to the gaseous hydrogen chloride.

In the case of the batchwise method, the total reaction time is from approx. 60 minutes to approx. 3 hours, including the time for the introduction of the hydrogen chloride.

After the reaction, the mixture is neutralized using a customary basic compound. Useful bases are in particular alkali metal hydroxides such as sodium hydroxide or potassium hydroxide, preferably as an aqueous solution, but also alkali metal carbonates or alkoxides. The use of alkali metal or alkaline earth metal alkoxides, in particular of sodium methoxide, sodium ethoxide, potassium methoxide or potassium ethoxide has the considerable advantage that this type of synthesis results in no wastewater. The alkoxides can be used in solid form, for example as powder or granules, or as an alcoholic solution.

The workup is effected in a manner known per se by removing the solid (crystalline) materials by a mechanical separating operation, such as a filtration or by centrifuging, and optionally washing them, or distillatively separating and purifying liquid products, depending on the purity requirements.

Examples of useful solvents for washing include alcohols having from 1 to 6 carbon atoms (e.g. methanol, ethanol, isopropanol) or ethers, as long as they are peroxide-free, for example methyl tert-butyl ether or tetrahydrofuran. The ketalization of triacetonamine with gaseous hydrogen chlorides has significant advantages:

Compared to a reaction with concentrated hydrochloric acid, the reaction of triacetonamine with the hydroxyl derivative and hydrogen chloride gas can be carried out quantitatively without any problems. For instance, the reactions of triacetonamine with ethylene glycol and concentrated aqueous hydrochloric acid which have been carried out as comparative experiments showed that as soon as excess water (and therefore excess hydrogen chloride) had been removed, the reaction mixture has attained a pH of only 4-5 and the conversion remained at approx. 80-85%. Even when p-toluenesulfonic acid was added and water was repeatedly removed, complete conversion of triacetonamine could not be achieved.

Triacetonamine is ketalized substantially faster using hydrogen chloride gas as the acid compared to reaction using concentrated aqueous hydrochloric acid, since the excess amount of water does not first have to be removed again from the reaction mixture. It is therefore possible by the process according to the invention to achieve a substantially higher space-time yield in comparison to the use of concentrated aqueous hydrochloric acid.

Comparative experiments have shown that when sulfuric or phosphoric acid is used as the catalyst, considerable amounts of by-products are formed, which can presumably be attributed to a decomposition of triacetonamine. This by-product formation is avoided by the process of the present invention.

The waste occurring in the process according to the invention after neutralization with a base is only the corresponding chloride salt (for example sodium chloride) which can be disposed of significantly better (or less expensively) than other salts, for example sodium sulfate, sodium phosphate or the corresponding sulfonic acid salt.

Hydrogen chloride gas is inexpensive, can be metered accurately and is often available via a gas line on the industrial scale. As a consequence, hydrogen chloride gas can be easily handled and incurs virtually no storage costs.

EXAMPLES

Example 1

Preparation of 2-(hydroxymethyl)-7,7,9,9-tetramethyl-1,4-dioxa-8-azaspiro[4.5]decane 155 g of triacetonamine were initially charged in 500 ml of toluene together with 184 g of glycerol. Subsequently, hydrogen chloride gas was introduced into the reactor via an immersed pipe, while maintaining the bottom temperature below 80° C. As soon as the hydrogen chloride uptake reduced distinctly, the reaction mixture was heated to reflux temperature and the water of reaction formed was removed on a water separator.

As soon as complete TAA conversion had been achieved, the reaction mixture was allowed to cool and adjusted to a pH of 11 by adding 200 g of 25% NaOH solution and 47 g of water. The precipitated product was filtered off with suction through a glass suction filter, washed in succession with water and isopropanol and dried under reduced pressure. The product was obtained as a white, free-flowing solid.

| | |
|---|---|
| Yield: | 175 g (76%) |
| Melting point: | 136-138° C. |

Example 2

Preparation of 7,7,9,9-tetramethyl-1,4-dioxa-8-azaspiro[4.5]decane 248 g of triacetonamine were initially charged in 500 ml of toluene together with 199 g of ethylene glycol. Subsequently, hydrogen chloride gas was introduced into the reactor via an immersed pipe, while maintaining the bottom temperature below 80° C. As soon as the hydrogen chloride uptake reduced distinctly, the reaction mixture was heated to reflux temperature and the water of reaction formed was removed on a water separator.

As soon as complete TAA conversion had been achieved, the reaction mixture was allowed to cool and adjusted to a pH of 11 by adding 303 g of 25% NaOH solution and 76 g of water. After separating the phases, the aqueous phase was extracted 3 times with toluene. The combined organic phases were fractionally distilled under reduced pressure.

| | |
|---|---|
| Yield: | 217 g (90%) |
| Boiling point: | 83° C./5 mbar |

Example 3

Preparation of 2-butyl-7,7,9,9-tetramethyl-1,4-dioxa-8-azaspiro[4.5]decane 248 g of triacetonamine were initially charged in 500 ml of toluene together with 378 g of 1,2-hexanediol. Subsequently, hydrogen chloride gas was introduced into the reactor via an immersed pipe, while maintaining the bottom temperature below 80° C. As soon as the hydrogen chloride uptake reduced distinctly, the reaction mixture was heated to reflux temperature and the water of reaction formed was removed on a water separator.

As soon as complete TAA conversion had been achieved, the reaction mixture was allowed to cool and adjusted to a pH of 11 by adding 303 g of 25% NaOH solution and 76 g of water. After separating the phases, the aqueous phase was extracted 3 times with toluene. The combined organic phases were fractionally distilled under reduced pressure.

| | |
|---|---|
| Yield: | 322 g (79%) |
| Boiling point: | 92° C./0.5 mbar |

Example 4

Preparation of 8,8,10,10-tetramethyl-1,5-dioxa-9-azaspiro[5.5]undecane 248 g of triacetonamine were initially charged in 500 ml of toluene together with 243 g of 1,3-propanediol. Subsequently, hydrogen chloride gas was introduced into the reactor via an immersed pipe, while maintaining the bottom temperature below 80° C. As soon as the hydrogen chloride uptake reduced distinctly, the reaction mixture was heated to reflux temperature and the water of reaction formed was removed on a water separator.

As soon as complete TAA conversion had been achieved, the reaction mixture was allowed to cool and adjusted to a pH of 11 by adding 303 g of 25% NaOH solution and 76 g of water. After separating the phases, the aqueous phase was extracted 3 times with toluene. The combined organic phases were fractionally distilled under reduced pressure.

| | |
|---|---|
| Yield: | 287 g (84%) |
| Boiling point: | 72° C./0.5 mbar |

Comparative Example 1

Preparation of 8,8,10,10-tetramethyl-1,5-dioxa-9-azaspiro[5.5]undecane

Use of Sulfuric Acid 155 g of triacetonamine were initially charged in 800 ml of toluene together with 124 g of ethylene glycol. Subsequently, sufficient sulfuric acid (106 g) was added that the reaction mixture showed an acidic pH ($\leqq 2$) when tested with a moistened indicator paper. The reaction mixture was heated to reflux temperature and water of reaction formed was removed on a rotary evaporator. After approx. 45 minutes, large amounts of a water-insoluble solid precipitated out and collected as sticky deposits on the flask and stirrer.

Comparative Example 2

Preparation of 8,8,10,10-tetramethyl-1,5-dioxa-9-azaspiro[5.5]undecane

Use of Phosphoric Acid 77 g of triacetonamine were initially charged in 240 g of toluene together with 47 g of ethylene glycol. Subsequently, sufficient phosphoric acid (63 g) was added that the reaction mixture showed an acidic pH ($\leqq 2$) when tested with a moistened indicator paper. The reaction mixture was heated to reflux temperature and water of reaction formed was removed on a water separator. After approx. 3 hours, there was less than 10% of the desired product according to the gas chromatogram. Instead, a plurality of secondary components had formed which were not investigated further.

Comparative Example 3

Preparation of 8,8,10,10-tetramethyl-1,5-dioxa-9-azaspiro[5.5]undecane

Use of Concentrated Aqueous Hydrochloric Acid 93 g of triacetonamine were initially charged in 190 ml of toluene together with 75 g of ethylene glycol and 65 g of concentrated hydrochloric acid. The reaction mixture was heated to reflux temperature and the water of reaction formed was removed on a water separator. It was found that the pH of the liquid phase had fallen from initially 1 to 4-5. As soon as this pH had been attained, the conversion remained at approx. 80-85%. After adding p-toluenesulfonic acid as a catalyst and removing water again, the conversion could be increased slightly, although even after adding and removing water three times, quantitative TAA conversion was not achieved.

The present application claims priority to DE 10304055.2 filed Feb. 1, 2003, the contents of which are incorporated herein by reference.

What is claimed is:

1. A process for ketalizing triacetonamine, which comprises:
reacting triacetonamine and a hydroxyl derivative having one or more hydroxyl groups with gaseous hydrogen chloride in a non-polar solvent to yield the open-chain or cyclic triacetonamine ketal.

2. The process as claimed in claim 1, wherein the solvent is an acyclic hydrocarbon, a cyclic hydrocarbon, or an aromatic hydrocarbon.

3. The process as claimed in claim 1, wherein the solvent is heptane, cyclohexane, ethylcyclohexane, toluene or xylene.

4. The process as claimed in claim 1, wherein the reacting is carried out at from 20° C. to 150° C.

5. The process as claimed in claim 1, wherein the reacting is carried out at from 50° C. to 90° C.

6. The process as claimed in claim 1, wherein the reacting forms water which is removed from the reaction mixture.

7. The process as claimed in claim 1, wherein triacetonamine and the hydroxyl derivative having one hydroxyl group are in a ratio of 1:2-8.

8. The process as claimed in claim 1, wherein triacetonamine and the hydroxyl derivative having one hydroxyl group are in a ratio of 1:2-4.

9. The process as claimed in claim 1, wherein the hydroxyl derivative has at least two hydroxyl groups.

10. The process as claimed in claim 9, wherein the triacetonamine and the hydroxyl derivative having at least two hydroxyl groups are in a ratio of 1:1-4.

11. The process as claimed in claim 9, wherein the triacetonamine and the hydroxyl derivative having at least two hydroxyl groups are in a ratio of 1:1-2.

12. The process as claimed in claim 1, wherein the hydroxyl derivatives are monohydric or polyhydric alcohols.

13. The process as claimed in claim 12, wherein the hydroxyl derivative is ethylene glycol or glycerol.

14. The process as claimed in claim 1, which further comprises adding superstoichiometric amounts of hydrogen chloride.

15. The process as claimed in claim 14, wherein the reacting is carried out batchwise, and the gaseous hydrogen chloride is added subsequently.

16. The process as claimed in claim 1, which further comprises neutralizing the reaction with an alkali metal alkoxide or alkaline earth metal alkoxide.

17. The process as claimed in claim 16, wherein the reaction mixture is neutralized with a powder or alcoholic form of sodium methoxide, sodium ethoxide, potassium methoxide or potassium ethoxide.

18. The process as claimed in claim 1, wherein the reaction is carried out continuously.

19. A process for producing a polymer, comprising ketalizing triacetonamine according to the process of claim 1, and adding the open-chain or cyclic triacetonamine to a polymerization reaction.

20. The process as claimed in claim 1, wherein the reacting is carried out with gaseous hydrogen chloride as the only catalyst.

21. The process as claimed in claim 1, wherein the reacting is carried out to convert at least 80% by weight of the triacetonamine to the open-chain or cyclic triacetonamine ketal.

22. The process as claimed in claim 1, wherein no further acid catalyst is used.

23. A process for ketalizing triacetonamine, which comprises:
reacting triacetonamine and a hydroxyl derivative having one or more hydroxyl groups with gaseous hydrogen chloride in a solvent to yield the open-chain or cyclic triacetonamine ketal,
wherein the solvent is an acyclic hydrocarbon, a cyclic hydrocarbon, or an aromatic hydrocarbon,
wherein the reacting forms water which is removed from the reaction mixture, and
wherein the reacting is carried out with gaseous hydrogen chloride as the only catalyst.

* * * * *